(12) United States Patent  
Fan et al.

(10) Patent No.: US 8,463,379 B2
(45) Date of Patent: Jun. 11, 2013

(54) LEAD WIRE AND PACEMAKER USING THE SAME

(75) Inventors: Li Fan, Beijing (CN); Wen-Mei Zhao, Beijing (CN); Chen Feng, Beijing (CN); Li Qian, Beijing (CN); Yu-Quan Wang, Beijing (CN); Liang Liu, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/339,450

(22) Filed: Dec. 29, 2011

(65) Prior Publication Data

US 2013/0103107 A1 Apr. 25, 2013

(30) Foreign Application Priority Data

Oct. 21, 2011 (CN) .......................... 2011 1 0322684

(51) Int. Cl.
*A61N 1/00* (2006.01)

(52) U.S. Cl.
USPC ............................................................ 607/9

(58) Field of Classification Search
USPC ..................... 607/9, 119; 977/904, 925, 931
See application file for complete search history.

(56) References Cited

U.S. PATENT DOCUMENTS 7,596,415 B2 * 9/2009 Brabec et al. ................. 607/121

* cited by examiner

*Primary Examiner* — George Manuel
(74) *Attorney, Agent, or Firm* — Altis Law Group, Inc.

(57) ABSTRACT

A lead wire and a pacemaker using the lead wire are disclosed. The lead wire, comprising: a lead body and a lead electrode at an end of the lead body, the lead electrode being electrically connected with the lead body, the lead electrode comprising a carbon nanotube structure, the carbon nanotube structure comprising at least one carbon nanotube film, the carbon nanotube structure having an electrode tip away from the lead body, and the electrode tip being in linear contact with an organ, wherein the electrode tip functions as a stimulating electrode, the at least one carbon nanotube film acts as a sensing electrode.

20 Claims, 6 Drawing Sheets ably implanted.

LEAD WIRE AND PACEMAKER USING THE SAME

RELATED APPLICATIONS

This application claims all benefits accruing under 35 U.S.C. §119 from China Patent Application No. 201110322684.3, filed on Oct. 21, 2011 in the China Intellectual Property Office, the disclosure of which is incorporated herein by reference.

BACKGROUND

1. Technical Field

The present disclosure relates to a lead wire and a pacemaker using the lead wire.

2. Discussion of Related Art

In generally, pacemakers are electronic therapeutic devices which can be implanted into human bodies. The pacemakers can emit pulse currents to stimulate tissues of organs which are not healthy to treat illnesses of the organs.

Lead wires are important elements in the pacemakers. The lead wires can provide pulse signals to the organs, and sense intrinsic activities of the organs for a purpose of suppressing pulse signals whenever a natural activity occurred within a predetermined time period after the last natural activity or a pulse signal. Thus the lead wires serve as both stimulating electrodes to provide pulse signals and sensing electrodes to electrically sense the intrinsic activities of organs.

The requirements for an optimum stimulating electrode and an optimum sensing electrode are sometimes conflicting. For example, the optimum stimulating electrode should have a very small surface area exposed to the heart tissue in order to achieve a low pacing threshold and a high current density. The sensing electrode requires a large surface area exposed to the heart tissue in order to detect a relatively low level electrical signal indicating natural heartbeat activities. However, the lead wires have a same working surface to function as the sensing electrode and the stimulating electrode, which may not meet the requirements of the sensing electrode and the stimulating electrode at the same time. Thus, the pulse signals and the sensing signals may not be accurate and reliable, making the pacemakers using lead wires inaccurate and unreliable.

What is needed, therefore, is to provide a lead wire and a pacemaker using the same, which can overcome the shortcomings as discussed above.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
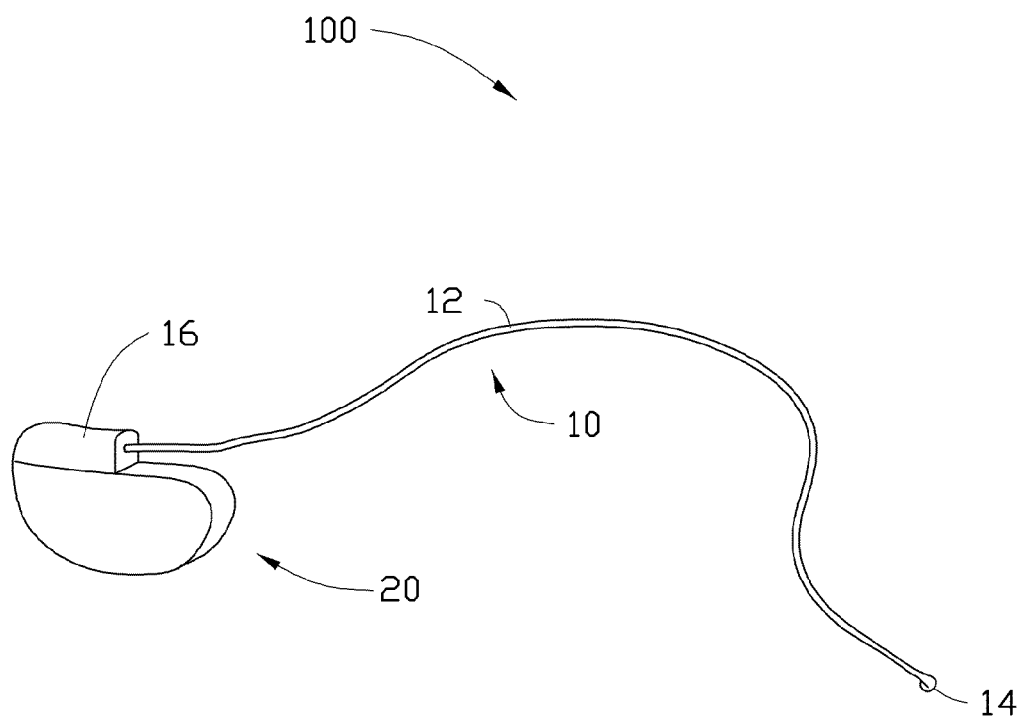
FIG. 1 is a schematic view of one embodiment of a heart pacemaker including a lead wire.

Referring to FIG. 1, one embodiment of a pacemaker 100 is provided. According to an application location of the pacemaker 100, the pacemaker 100 can be a cardiac pacemaker, a brain pacemaker, an ear pacemaker, a gastric pacemaker, or a chest pacemaker. The pacemaker 100 comprises a lead wire 10 and a pulse generator 20 electrically connected with the lead wire 10. The lead wire 10 can be used to transfer signals generated by the pulse generator 20 and an organ. The organ can be heart, brain, chest, ear or stomach. In one embodiment, the organ is a heart, and the pacemaker 100 is a cardiac pac The pulse generator 20 usually comprises a shell (not labeled), a power source (not shown) and a control circuit (not shown). The power source and the control circuit are both received in the shell. A material of the shell can be metal, which is compatible with the organ. In one embodiment, the material of the shell is titanium alloy. The power source provides energy for the control circuit, and can be a chemical cell, such as a lithium cell or a fuel cell. In one embodiment, the power source is a lithium-iodine cell. The control circuit can comprise an output circuit generating pulse signals and an input circuit. The input circuit can sense electrical signals of the organ and transfer the electrical signals to the output circuit, such that suitable pulse signals are transferred to the organ. The pulse signals can be a rectangular pulse current with a pulse width ranging from about 0.5 ms to about 0.6 ms. The pulse current works by charge and discharge of a capacitor in the control circuit.

The lead wire 10 comprises a lead body 12, a lead electrode 14 and a connector 16. The lead body 12 has two opposite ends. The lead electrode 14 is located at one end of the lead body 12. The connector 16 is located another end of the lead body 12. The lead body 12 has a good electrically conductivity, and is mainly used to transfer signals between the pulse generator 20 and the lead electrode 14. The lead electrode 14 contacts with the organ, and electrically connects with the lead body 12. The connector 16 connects the lead body 12 with the pulse generator 20, and couples with a connecting part of the pulse generator 20.

Figure 2:
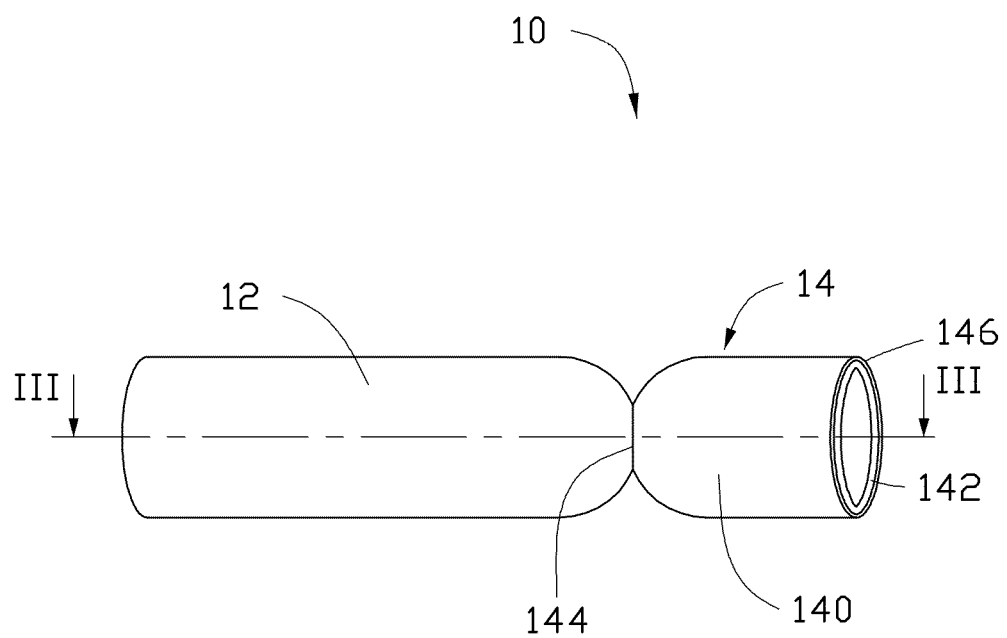
FIG. 2 is a schematic view of the lead wire shown in FIG. 1.
Figure 3:
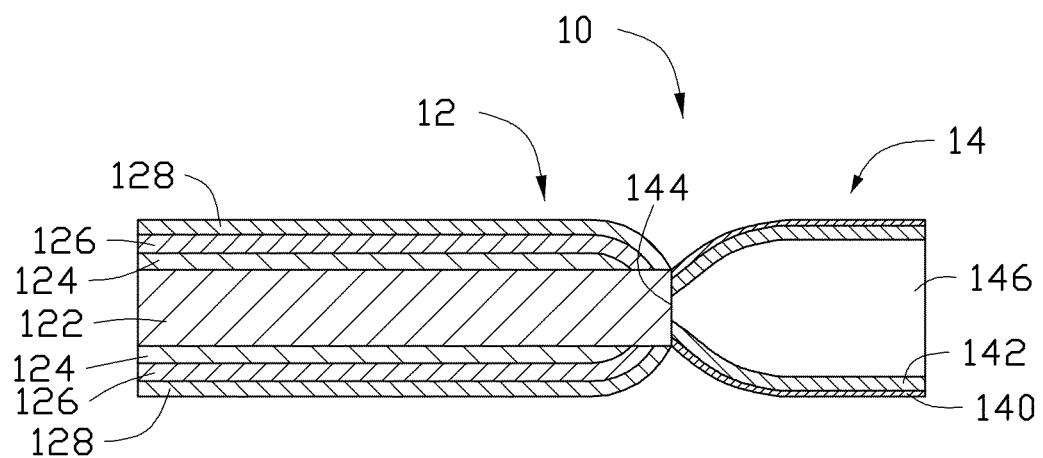
FIG. 3 is a cross-sectional view of the lead wire along line III-III shown in FIG. 2.

Also referring to FIGS. 2 and 3, the lead electrode 14 is connected with the lead body 12 by an electrical conductive adhesive or a soldering method. The lead electrode 14 comprises a carbon nanotube structure 140. The carbon nanotube structure 140 comprises a side part (not labeled), a connected end 144, and an electrode tip 146. The side part is separated from the organ. The connected end 144 and the electrode tip 146 are respectively located on two opposite ends of the side part. The connected end 144 is electrically contacted with the lead body 12. The electrode tip 146 is in linear contact with the organ. The carbon nanotube structure 140 can be a sheet-shaped structure or a hollow structure formed by curved the sheet-shaped structure. The hollow structure having an open end can be a hollow barrel-shaped structure, a hollow conical structure, a hollow pyramid-shaped structure, a hollow truncated-cone-shaped structure, or other hollow stereo structure.

A shape of the open end of the hollow structure can be circle, rectangle, square, triangle, ellipse, or other close structure.

The carbon nanotube structure 140 is a porous structure with electrical conductivity. The carbon nanotube structure 140 as a whole has a large surface area, which can satisfy the demand of a sensing electrode to sense signals of the organ. The carbon nanotube structure 140 acts as the sensing electrode, that is, both the side part and the electrode tip 146 of the carbon nanotube structure 140 act as the sensing electrode. The electrode tip 146 is in linear contact with the organ. The electrode tip 146 of the carbon nanotube structure 140 has a small surface area, which can satisfy the demand of a stimulating electrode, thus, the electrode tip 146 acts as the stimulating electrode to provide pulse signals for the organ. The carbon nanotube structure 140 used in the lead electrode 14 can improve the work surface of the sensing electrode, and relatively reduce the work surface of the stimulating electrode. Thus, the carbon nanotube structure 140 can both satisfy the demands of the sensing electrode and the stimulating electrode, which makes the lead wire 10 perform sensing function and stimulating function in sequence. Therefore, the accuracy and reliability of the pulse signals and the sensing signals can be improved, as such, the accuracy and reliability of the pacemaker 100 using the lead wire 10 can also be improved.

The carbon nanotube structure 140 comprises a number of carbon nanotubes and defines a number of pores by the carbon nanotubes. The effective diameters of the micropores are in a range from about 1 nanometer (nm) to about 450 nm. The carbon nanotubes combine with each other by Van der Waals force, which makes the carbon nanotube structure have a specific shape and be a free standing structure. The term "free-standing structure" comprises, but is not limited to, a structure capable of being supported by itself and does not need support from a substrate. For example, the carbon nanotube structure 140 can be lifted by one point thereof such as a corner or a frame without sustaining damage under its own weight.

The carbon nanotube structure 140 comprises at least one carbon nanotube film. The carbon nanotube film can be formed by ordered or disordered carbon nanotubes. The ordered carbon nanotube film consists of ordered carbon nanotubes. Ordered carbon nanotube films comprise films on which the carbon nanotubes are substantially arranged along a primary direction. Examples comprise films wherein the carbon nanotubes are arranged approximately along a same direction or have two or more sections within each of which the carbon nanotubes are arranged approximately along a same direction (different sections can have different directions). The carbon nanotube film may be a drawn carbon nanotube film, pressed carbon nanotube film, or flocculated carbon nanotube film.

Drawn Carbon Nanotube Film

Figure 4:
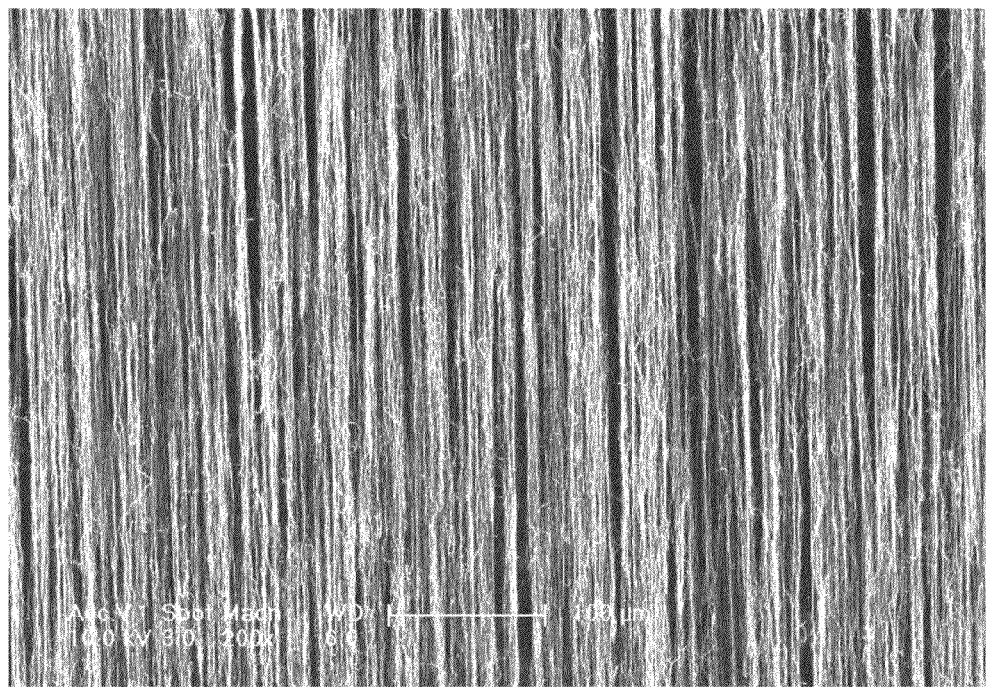
FIG. 4 shows a scanning electronic microscope (SEM) image of a drawn carbon nanotube film used in FIG. 2.

Referring to FIG. 4, the carbon nanotubes in the drawn carbon nanotube film are oriented along a same preferred orientation and are approximately parallel to each other. In this connection, the term "approximately" as used herein means that it is impossible and unnecessary that every carbon nanotube in the carbon nanotube films are parallel to each other, because factors, such as a change in drawing speed or non-uniform drawing force on the carbon nanotube film when the carbon nanotube film is drawn from a carbon nanotube array, can affect the orientation of the carbon nanotubes. A drawn carbon nanotube film can be drawn from a carbon nanotube array to form the ordered carbon nanotube film. Examples of drawn carbon nanotube film are taught by U.S. Pat. No. 7,045,108 to Jiang et al. The drawn carbon nanotube film comprises a plurality of successive and oriented carbon nanotubes joined end-to-end by van der Waals force therebetween. The drawn carbon nanotube film is a free-standing film. The carbon nanotube film can be treated with an organic solvent to increase the mechanical strength of the carbon nanotube film and reduce the coefficient of friction of the carbon nanotube film. A thickness of the carbon nanotube film can range from about 0.5 nm to about 100 μm.

Understandably, the carbon nanotube film structure may further comprise at least two stacked carbon nanotube films. Additionally, when the carbon nanotubes in the carbon nanotube film are aligned along one preferred orientation (e.g., the drawn carbon nanotube film), an angle can be formed between the orientation of carbon nanotubes in adjacent films. Adjacent carbon nanotube films can only be combined by the van der Waals force therebetween. The number of the layers of the carbon nanotube films is not limited. However the specific surface area will decrease as the thickness of the carbon nanotube structure increases. An angle between the aligned axes of the carbon nanotubes in two adjacent carbon nanotube films can range from about 0 degrees to about 90 degrees.

Pressed Carbon Nanotube Film

Figure 5:
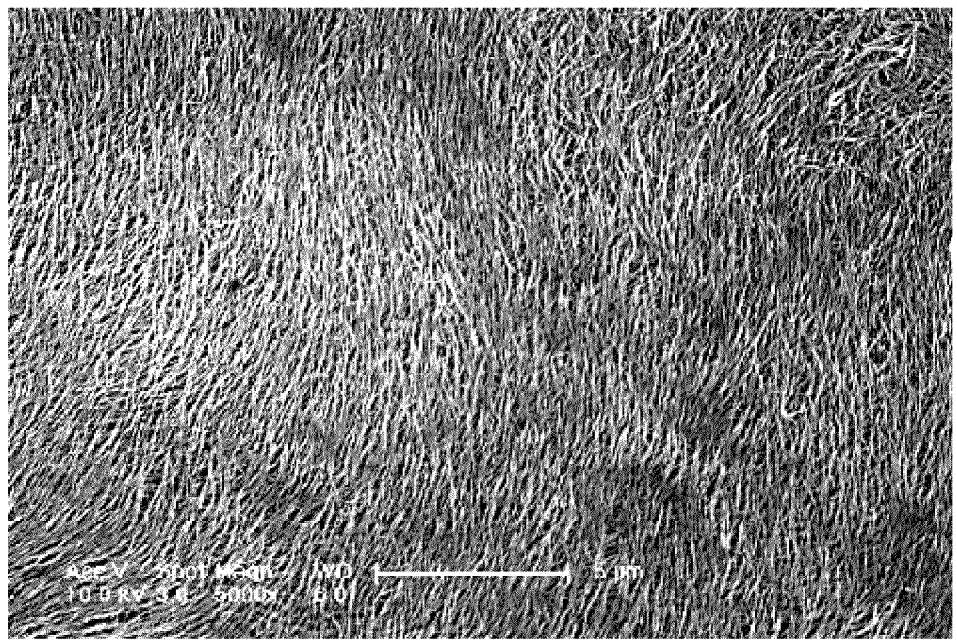
FIG. 5 shows an SEM image of a pressed carbon nanotube film used in FIG. 2.

Referring to FIG. 5, the ordered carbon nanotube film may be a pressed carbon nanotube film defining a number of regions. Each of the regions comprises a number of carbon nanotubes substantially oriented along the same direction. The carbon nanotubes in the pressed carbon nanotube film can rest upon each other. Adjacent carbon nanotubes are attracted to each other and combined by van der Waals force. In one embodiment, the angle between a primary alignment direction of the carbon nanotubes and a surface of the pressed carbon nanotube film is 0 degrees to approximately 15 degrees, with the angle decreasing with increasing applied pressure. The thickness of the pressed carbon nanotube film can range from about 0.5 nm to about 1 mm. Examples of a pressed carbon nanotube film are taught in US application 2008/0299031A1 to Liu et al. The pressed carbon nanotube film can be formed by providing an array of carbon nanotubes forming a substrate, and providing pressure on the array of carbon nanotubes.

The pressed carbon nanotube film also may be a disordered carbon nanotube film, which has a number of carbon nanotubes arranged along different directions. The pressed carbon nanotube film can be a free-standing carbon nanotube film. When the carbon nanotubes in the pressed carbon nanotube film are arranged along different directions, some properties of the pressed carbon nanotube film along directions parallel with a surface of the pressed carbon nanotube film can be the same, such as, conductivity, intensity, etc. The, thickness of the pressed carbon nanotube film ranges from about 0.5 nm to about 1 mm. Examples of the pressed carbon nanotube film are taught by US application 2008/0299031A1 to Liu et al.

Flocculated Carbon Nanotube Film

Figure 6:
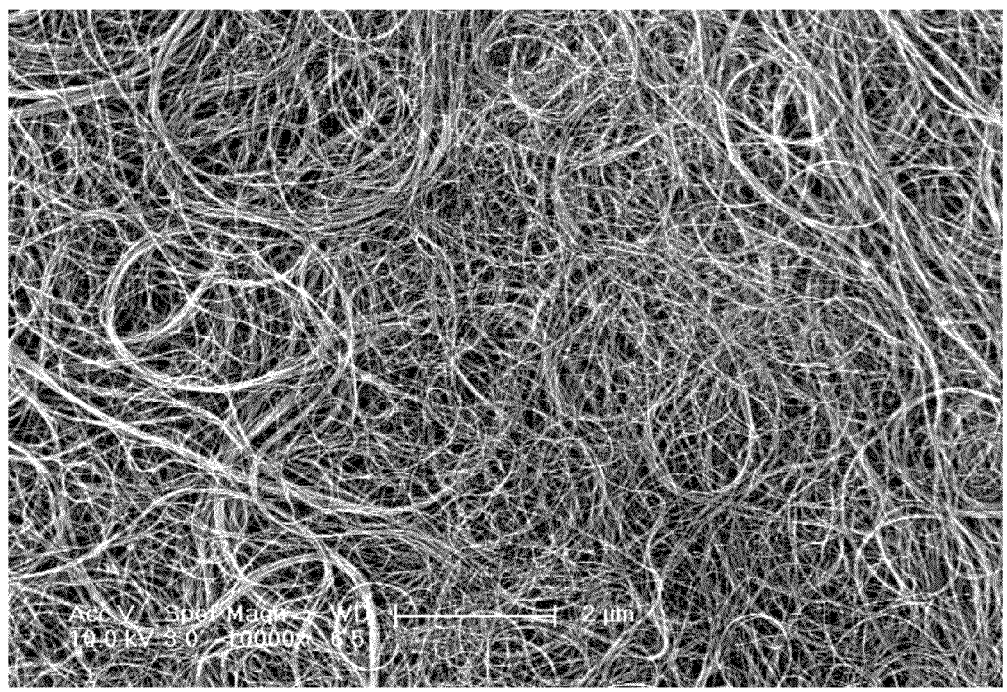
FIG. 6 shows an SEM image of a flocculated carbon nanotube film used in FIG. 2.

Referring to FIG. 6, the disordered carbon nanotube film consists of the carbon nanotubes arranged in a disorderly fashion. Disordered carbon nanotube films comprise randomly aligned carbon nanotubes. If the disordered carbon nanotube film comprises a film wherein the number of the carbon nanotubes aligned in every direction is substantially equal, some properties of the flocculated carbon nanotube film along directions parallel with a surface of the flocculated carbon nanotube film can be the same, such as, conductivity, intensity, etc. The disordered carbon nanotubes can be entangled with each other and/or be substantially parallel to a surface of the disordered carbon nanotube film. The disordered carbon nanotube film may be a flocculated carbon nanotube film. The flocculated nanotube film is also a freestanding structure. The flocculated carbon nanotube film can comprise a plurality of long, curved, disordered entangled carbon nanotubes. The carbon nanotubes can be substantially uniformly dispersed in the flocculated carbon nanotube film. Adjacent carbon nanotubes are attracted by van der Waals force to form an entangled structure with micropores defined therein. It is understood that the flocculated carbon nanotube film is porous. Effective diameters of the micropores can be less than 10 μm. Because the carbon nanotubes in the flocculated carbon nanotube film are entangled, the carbon nanotube structure employing the flocculated carbon nanotube film has excellent durability, and can be fashioned into desired shapes with a low risk to the integrity of the flocculated carbon nanotube film. The thickness of the flocculated carbon nanotube film can range from about 0.5 nm to about 1 mm. The flocculated carbon nanotube film can be provided by flocculating carbon nanotubes in a solvent to acquire a flocculated carbon nanotube structure, separating the flocculated carbon nanotube structure from the solvent, and shaping the separated flocculated carbon nanotube structure into the flocculated carbon nanotube film in which the carbon nanotubes are entangled and some properties of the flocculated carbon nanotube film along directions parallel with a surface of the flocculated carbon nanotube film can be the same, such as, conductivity, intensity, etc.

A length and a width of the flocculated carbon nanotube film can be arbitrarily set according to need. A thickness of the flocculated carbon nanotube film can range from about 0.5 nm to about 100 mm. The carbon nanotubes in the flocculated carbon nanotube film can be single-walled, double-walled, multi-walled carbon nanotubes, or combinations thereof. The diameters of the single-walled carbon nanotubes, the double-walled carbon nanotubes, and the multi-walled carbon nanotubes can, respectively, be in a range from about 0.5 nm to about 50 nm, about 1 nm to about 50 nm, and about 1.5 nm to about 50 nm.

In one embodiment, the carbon nanotube structure 140 comprises at least one drawn carbon nanotube film. The carbon nanotubes in the at least one drawn carbon nanotube film are substantially oriented along a same direction. The at least one drawn carbon nanotube film can be coiled into a hollow structure along axial direction of the carbon nanotubes in the at least one drawn carbon nanotube film. Thus, a surface of the organ contacted with the electrode tip 146 is substantially perpendicular to the axial direction of the carbon nanotubes in the carbon nanotube structure. The carbon nanotubes have a good electrical conductivity, such that the electrode tip 146 also has a good electrical conductivity. Therefore, the electrode tip 146 is suitable as the stimulating electrode.

In one embodiment, the carbon nanotube structure 140 is consisted of ten drawn carbon nanotube films stacked with each other. Adjacent drawn carbon nanotube films are combined by Van der Waals force. The carbon nanotube structure 140 consists of a number of carbon nanotubes substantially extend along a same direction. The ten drawn carbon nanotube films are coiled into a hollow barrel-shaped structure along the axial direction of the carbon nanotubes. The ten drawn carbon nanotube films are fixed on the lead body 12 via soldered method. The connected end 144 of the carbon nanotube structure 140 is soldered on the lead body 12. The carbon nanotubes are substantially joined end-to-end along a direction of from the connected end 144 to the electrode tip 146, therefore the pulse signals generated from the pulse generator 20 are transferred from the connected end 144 to the electrode tip 146. The carbon nanotubes have an excellent conductivity along the direction of from the connected end 144 to the electrode tip 146. Thus, the pulse signals can be accurately and reliably transferred to the organ, the electrode tip 146 used as the stimulating electrode can improve the accuracy and the reliability of the pulse signals. The ten drawn carbon nanotube films have a large surface area because of their porous structure, therefore the ten drawn carbon nanotube films used as the sensing electrode can improve the accuracy and the reliability of the electrical signals generated from the organ.

The lead electrode 14 can further comprise a support 142 attached to the carbon nanotube structure 140. The support 142 supports the carbon nanotube structure 140 to ensure the carbon nanotube structure 140 does not deform and sufficiently contacts with the organ. Thus, the carbon nanotube structure 140 can effectively act as the sensing electrode and the stimulating electrode. The support 142 should have a certain strength and be compatible with the organ, whether the support 142 can electrically conduct or not. The support 142 can be fixed on the lead wire 10 by an adhesive or a mechanical method, such as a helicity coupling method, or a snap-fitting method. A shape of the support 142 is substantially the same as that of the carbon nanotube structure 140, and be a hollow structure or a sheet-shaped structure. In one embodiment, the support 142 and the carbon nanotube structure 140 both have hollow structures. The carbon nanotube structure 140 wraps on a surface of the support 142. An effective diameter of the carbon nanotube structure 140 is larger than that of the support 142 to make the carbon nanotube structure 140 expose to the organ.

The lead body 12 is a concentric linear structure. The lead body 12 comprises a lead core 122, a first insulated layer 124, a shield layer 126 and a second insulated layer 128. The first insulated layer 124 wraps around the lead core 122. The shield layer 126 wraps around the first insulated layer 124. The second insulated layer 128 wraps around the shield layer 126. The lead core 122 is electrically connected with the lead electrode 14, which functions as the sensing electrode and the stimulating electrode. The first and the second insulated layers 124, 128 respectively insulate the shield layer 126 from the lead core 122 and the organ. When the pacemaker 100 using the lead body 12 is in working status, a positive electrode of the power source in the pulse generator 20 is electrically connected with the shell of the pulse generator 20, a negative electrode of the power source is electrically connected with the control circuit in the pulse generator 20. The pulse generator 20 generates pulse signals. The lead body 12 transfers the pulse signals into the lead electrode 14 under the control circuit, then the electrode tip 146 of the lead electrode 14 transfers the pulse signals into the organ, thereby stimulating the organ. Potential differences between the carbon nanotube structure 140 and the shell of the pulse generator 20 can be monitored. The potential differences can reflect the activity of the organ, such as the beating frequency of heart. The potential differences are transferred to the control circuit, the control circuit can adjust the pulse signals provided to the organ, which makes the organ work normally.

It can be understood that the lead body 12 can comprise a number of the lead cores 122, a number of insulated layers, the shield layer 126, and at least one ring electrode. The lead cores 122 are insulated from each other by the insulated layers wrapping around the lead cores 122. One of the lead cores 122 is electrically connected with the lead electrode 14, the other lead cores 122 are in electrical contact with the at least one ring electrode. The at least one ring electrode is used for sensing physiological characteristics of the organ, such as oxygen content or pressure in the organ. In one embodiment, the lead body 12 comprises two lead cores 122 and one ring electrode. One of the lead cores 122 is connected with the lead electrode 14 and the control circuit in the pulse generator 20, the other lead core 122 is electrically connected with the ring electrode and a positive electrode of the power source in the pulse generator 20. It can be understood that the number of the lead core 122 in the lead body 12 is determined by the number of ring electrode.

The lead core 122 has a good electrical conductivity, a material of the lead core 122 can be MP35N, 35NLT, stainless steel, carbon fiber, tantalum, titanium, zirconium, niobium, titanium alloy, copper, silver, platinum, platinum-yttrium alloy, or platinum-palladium alloy. Wherein, MP35N is an alloy including 35Co-35Ni-20Cr-10Mo, and titanium has a weight percentage of about 1% in the MP35N. 35NLT is also an alloy including 35Co-35Ni-20Cr-10Mo, titanium has a weigh percentage of about 0.01% in the 35NLT. The material of the lead core 122 also can be carbon nanotubes, the lead core 122 can be carbon nanotube wires composed of the carbon nanotubes. The first and the second insulated layers 124, 128 have an excellent electrical insulation, and can be made of silicone, polyesterimide, polytetrafluoroethylene, or other insulated materials which are compatible with the organ. A material of the shield layer 126 can be MP35N, 35NLT, carbon nanotubes, or other electrical conductive materials. In one embodiment, the lead core 122 is made of platinum-yttrium alloy, the material of the insulated layer is polytetrafluoroethylene, and the shield layer is composed of carbon nanotubes.

It is to be understood that the above-described embodiment is intended to illustrate rather than limit the disclosure. Variations may be made to the embodiment without departing from the spirit of the disclosure as claimed. The above-described embodiments are intended to illustrate the scope of the disclosure and not restricted to the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. A lead wire, comprising: a lead body and a lead electrode at an end of the lead body, the lead electrode being electrically connected with the lead body, the lead electrode comprising a carbon nanotube structure, the carbon nanotube structure comprising at least one carbon nanotube film, an end of the carbon nanotube structure being an electrode tip away from the lead body, and the electrode tip capable of linearly contacting with an organ, wherein the electrode tip functions as a stimulating electrode, the carbon nanotube structure acts as a sensing electrode.

2. The lead wire of claim 1, wherein the carbon nanotube structure further comprises a connected end and a side part, the side part connects the connected end and the electrode tip, the lead body is connected to the carbon nanotube structure at the connected end.

3. The lead wire of claim 1, wherein the carbon nanotube structure is a sheet-shaped structure.

4. The lead wire of claim 1, wherein the carbon nanotube structure is a hollow barrel-shaped structure, a hollow conical structure, a hollow pyramid-shaped structure, or a hollow truncated-cone-shaped structure by coiling the at least one carbon nanotube film.

5. The lead wire of claim 1, wherein the carbon nanotube structure is a free-standing structure having a plurality of pores.

6. The lead wire of claim 5, wherein each of the at least one carbon nanotube film of the carbon nanotube structure comprises a plurality of carbon nanotubes substantially extending along a same direction.

7. The lead wire of claim 6, wherein the plurality of carbon nanotubes are joined end-to-end by Van der Waals forces in the same direction.

8. The lead wire of claim 7, wherein the at least one carbon nanotube film comprises a plurality of carbon nanotube films stacked on each other.

9. The lead wire of claim 5, wherein each of the at least one carbon nanotube film of the carbon nanotube structure comprises a plurality of carbon nanotubes entangled into a net structure by Van der Waals force.

10. The lead wire of claim 5, wherein the at least one carbon nanotube film defines a plurality of regions, each of the plurality of regions comprises a plurality of carbon nanotubes substantially extending along a same direction.

11. The lead wire of claim 1, wherein the lead electrode further comprises a support, the at least one carbon nanotube film is attached to the support.

12. The lead wire of claim 11, wherein the support is fixed on the end of the lead body by spiral coupling, snap-fitting, or an adhesive.

13. A pacemaker capable of contacting with an organ, comprising:
a lead wire comprising a lead body and a lead electrode located at one end of the lead body, the lead electrode being electrically connected with the lead body; and
a pulse generator providing a pulse signal for the lead wire;
wherein the lead electrode comprises a carbon nanotube structure configured to be acted as a sensing electrode, the carbon nanotube structure comprises at least one carbon nanotube film, an end of the carbon nanotube structure is an electrode tip away from the lead body, and the electrode tip is capable of being linearly contacting with the organ and configured to be acted as a stimulating electrode.

14. The pacemaker of claim 13, wherein the carbon nanotube structure further comprises a connected end and a side part, the side part connects the connected end and the electrode tip, the lead body is connected to the carbon nanotube structure at the connected end.

15. The pacemaker of claim 14, wherein the carbon nanotube structure comprises a plurality of carbon nanotubes substantially oriented along a direction from the connected end to the electrode tip.

16. The pacemaker of claim 14, wherein the carbon nanotube structure is a sheet-shaped structure, a hollow barrel-shaped structure, a hollow conical structure, a hollow pyramid-shaped structure, or a hollow truncated-cone-shaped structure; wherein the hollow barrel-shaped structure, the hollow conical structure, the hollow pyramid-shaped structure, and the hollow truncated-cone-shaped structure are formed by coiling the sheet-shaped structure.

17. The pacemaker of claim 13, wherein the carbon nanotube structure is a free-standing structure having a plurality of pores.

18. The pacemaker of claim 17, wherein the at least one carbon nanotube film of the carbon nanotube structure comprises a plurality of carbon nanotubes substantially extending along a same direction.

19. The pacemaker of claim 18, wherein the plurality of carbon nanotubes are joined end-to-end by Van der Waals forces in the same direction.

20. The pacemaker of claim 13, wherein the lead electrode further comprises a support, the carbon nanotube structure is attached to the support, and the support is fixed on the end of the lead body.

* * * * *